United States Patent [19]

Kummer et al.

[11] Patent Number: 4,619,790
[45] Date of Patent: Oct. 28, 1986

[54] MANUFACTURE OF HIGHER ALKYLCARBOXYLIC ACIDS

[75] Inventors: Rudolf Kummer, Frankenthal; Kurt Schwirten, Ludwigshafen, both of Fed. Rep. of Germany

[73] Assignee: BASF Aktiengesellschaft, Ludwigshafen, Fed. Rep. of Germany

[21] Appl. No.: 874,316

[22] Filed: Feb. 1, 1978

[30] Foreign Application Priority Data

Mar. 4, 1977 [DE] Fed. Rep. of Germany ....... 2709438

[51] Int. Cl.$^4$ .................... C07C 51/14; C07C 53/126
[52] U.S. Cl. .............................. 260/413; 260/410.9 R; 560/233; 562/522; 568/451; 585/277
[58] Field of Search ............ 260/413, 533 A, 410.9 R; 560/232, 233; 562/522, 517, 518, 519

[56] References Cited

U.S. PATENT DOCUMENTS

| 2,448,368 | 8/1948 | Gresham et al. | 260/533 A |
| 2,768,968 | 10/1956 | Reppe et al. | 260/533 A |
| 2,854,458 | 9/1958 | Reppe et al. | 260/533 A |
| 2,911,422 | 11/1959 | Ercoli | 260/533 A |
| 2,916,513 | 12/1959 | Lautenschlager et al. | 560/522 |
| 3,023,237 | 2/1962 | Reppe et al. | 560/522 |
| 3,481,975 | 12/1969 | Rudkovsky et al. | 260/533 A |
| 3,906,016 | 9/1975 | Isa et al. | 560/233 |

FOREIGN PATENT DOCUMENTS 1281615  7/1972  United Kingdom ................ 560/233

Primary Examiner—Vivian Garner
Attorney, Agent, or Firm—Keil & Weinkauf

[57] ABSTRACT

Alkylcarboxylic acids (where alkyl is of 6 to 20 carbon atoms) are manufactured by hydrocarboxylating the corresponding olefins by means of cobalt carbonyl compounds in the presence of from 0.5 to 1.5 kg of N-methylpyrrolidone, per kg of the olefin, as the solvent.

3 Claims, No Drawings

MANUFACTURE OF HIGHER ALKYLCARBOXYLIC ACIDS

The present invention relates to an improved process for the manufacture of alkylcarboxylic acids (where alkyl is of 6 to 20 carbon atoms), by hydrocarboxylating the corresponding olefins of 6 to 20 carbon atoms. The hydrocarboxylation of olefins, in accordance with the following equation

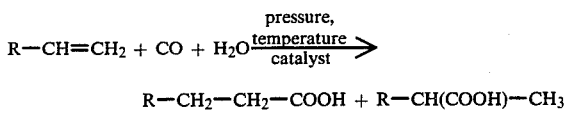

$$R-CH_2-CH_2-COOH + R-CH(COOH)-CH_3$$

R = alkyl
is a conventional process for the manufacture of alkylcarboxylic acids. Whilst this method has proved valuable for industrial purposes in the case of lower carboxylic acids, it has hitherto not gained acceptance for the manufacture of higher homologs, in the main because the olefin and water are barely miscible with one another even at elevated temperatures and for this reason only react with one another slowly, or with substantial formation of undesirable byproducts, above all if the process is carried out continuously. For example, carbon monoxide and water are converted to carbon dioxide and hydrogen under the reaction condtions, and consequently the olefins are in part hydrogenated to give paraffins and hydroformylated to give aldehydes.

In order to be able to carry out the reaction in a substantially homogeneous phase, it has therefore frequently been preferred (cf., for example, German Laid-Open Application DOS 1,618,156) to use alcohols instead of water for the carbonylation and to hydrolyze the esters, thus obtained in good yield, to the acids. However, it is obvious that this procedure is far removed from the economic optimum. Another variant, namely the addition of pyridine as a solubilizing agent, has also not proved successful, because the yield is unsatisfactory (cf., for example, Zh. Org. Khim., 2 (1966), 231 and 3 (1967), 242, and Zh. Prikl. Khim., 41 (1968), 172).

The above conventional syntheses relate to the use of cobalt carbonyl compounds as catalysts, since the nickel carbonyl compounds and noble metal carbonyl compounds which are also conventionally used for carbonylations give even less advantageous results when used for the hydrocarboxylation of the higher olefins, either in respect of the yield or because of the technical difficulties resulting from the volatility of nickel carbonyl or because of losses of noble metals, eg. palladium or rhodium.

It is an object of the present invention to improve the synthesis of alkylcarboxylic acids (where alkyl is of 6 to 20 carbon atoms) by hydrocarboxylation of the corresponding olefins, using cobalt carbonyl compounds as catalysts.

We have found that alkylcarboxylic acids (where alkyl is of 6 to 20 carbon atoms) are obtained, by hydrocarboxylating the corresponding olefins by means of cobalt carbonyl compounds in the presence of a solvent, in higher absolute yield and with a higher space-time yield if from 0.2 to 3 kg of N-methylpyrrolidone, per kg of the olefin, is used as the solvent.

Suitable starting compounds include both unbranched and branched olefins with a terminal or non-terminal double bond. According to the conventional rules, these olefins merely differ in reactivity, which generally decreases with increasing degree of branching and with increasing steric screening of the double bond. However, the lower reactivity of such olefins can be substantially counterbalanced by using more severe reaction conditions. Linear α-olefins react particularly easily and, as a result of the presence of N-methylpyrrolidone in accordance with the invention, predominantly give the N-alkylcarboxylic acids, which in the main are the desired products. In practice, the process is also of particular importance for hydrocarboxylating propylene and butylene oligomers, e.g., trimeric propylene, tetrameric propylene and diisobutylene. These are frequently isomer mixtures, so that the products obtained are also mixtures of isomeric carboxylic acids. In addition to the olefin oligomers already mentioned, preferred olefins are linear olefins and mixtures of olefins of 8 to 15 carbon atoms as obtained on cracking paraffin.

Apart from the presence of N-methylpyrrolidone, in accordance with the invention, the process is carried out under the conventional reaction conditions for hydrocarboxylation, i.e., under a CO pressure of from 100 to 1,000 bars and at a temperature of from 150° to 220° C. Again following the conventional method, from 1 to 2 moles of water and from 0.01 to 0.1 mole equivalent (expressed as cobalt) of the cobalt catalyst are used per mole of olefin. The cobalt can be employed in the form of dicobalt-octacarbonyl, but cobalt salts, e.g. cobalt acetate or cobalt palmitate (cobalt soaps) in general fulfil the same purpose, since the active carbonyl complexes are formed in situ under the reaction conditions. The cobalt salts (cobalt soaps) of the carboxylic acids formed during the process are particularly suitable.

Within the stated range of from 0.2 to 3 kg per kg of olefin, the preferred amount of N-methylpyrrolidone is from 0.5 to 1.5 kg/kg of olefin.

The process can be carried out batchwise but as a rule a continuous method is preferred, for economic and technological reasons. The procedure followed is, in general, to charge the reactor with the solution of the dicobalt-octacarbonyl in the olefin, and with aqueous N-methylpyrrolidone. If the cobalt is employed in the form of its salts, these can also be added to the aqueous solvent phase. After reaction of the starting materials under the above conditions, air is passed through the reaction mixture, whereby the cobalt compound is reconverted to the Co-II form. Instead of air, a different oxidizing agent, preferably hydrogen peroxide, can be used. The mixture is then subjected to fractional distillation. N-Methylpyrrolidone and unconverted olefin are recycled, as is the high-boiling residue which contains the cobalt and which, before introduction into the reactor, is advantageously dissolved in the olefin.

Depending on the starting olefin, the desired carboxylic acids are obtained in yields of from about 75 to 90%. From about 5 to 20% are accounted for by unconverted olefin and the remainder is in the form of by-products, including, above all, the paraffin corresponding to the olefin. Compared to the best conventional process, i.e. hydrocarboxylation in the presence of pyridine, the economics of the process, taking into account the yields, by-products and process costs, are throughout from about 10 to 50% better.

The higher alkylcarboxylic acids are in the main used for the manufacture of plasticizers, dryers and corrosion protection agents.

EXAMPLE 1

3,5,5-Trimethylhexanoic acid

Per hour, a solution of 154 g (=1.38 moles) of diisobutylene (2,4,4-trimethylpent-1-ene) and 154 g (=0.026 mole equivalent) of cobalt in the form of dicobaltoctacarbonyl, and a mixture of 218 g of N-methylpyrrolidone and 31.5 g (=1.75 mole) of water were fed to a high pressure autoclave having a capacity of 1.6 l and equipped with a lift-type stirrer. The autoclave was under a carbon monoxide pressure of 300 bars and the reaction temperature was 200° C.

According to analysis of the crude product by gas chromatography, the yield of 3,5,5-trimethylhexanoic acid was 78%. 15% of the olefin remained unchanged, 5% were hydrogenated to the paraffin and the remainder comprised aldehydes, esters and other by-products.

The mixture was then treated with 2.5 g of 30% strength hydrogen peroxide to destroy the carbonyl complex, after which it was fractionated. The yield of 3,5,5-trimethylhexanoic acid was 77%.

Using the same conditions, but with the optimum amount of 65 g of pyridine instead of N-methylpyrrolidone, the yield of carboxylic acid achieved was only about 25%. It is true that it was possible to increase this yield to 50% by raising the temperature to 220° C., but at this temperature as much as 15% of undesirable by-products was formed.

EXAMPLE 2 n-Tridecanoic acid

Using the method described in Example 1, a solution of 165 g (=0.98 mole) of dodec-1-ene and 1.65 g (=0.28 mole equivalent) of cobalt in the form of dicobaltoctacarbonyl, and a mixture of 157 g of N-methylpyrrolidone and 23 g (=1.28 mole) of water, were hydrocarboxylated under a CO pressure of 300 bars at 190° C. Conventional working up gave a yield of 83% of tridecanoic acid, of which 60% consisted of the particularly valuable n-isomer. 13% of the olefin had not reacted and the remainder consisted of by-products, including 2% of dodecane.

We claim:

1. A process for the manufacture of an alkylcarboxylic acid (where alkyl is of 6 to 20 carbon atoms) by hydrocarboxylating the corresponding olefin by means of a cobalt carbonyl compound in the presence of a solvent, wherein the solvent used is from 0.2 to 3 kg of N-methylpyrrolidone per kg of the olefin.

2. A process as set forth in claim 1, wherein the olefin is selected from the group consisting of propylene oligomers and butylene oligomers.

3. A process as set forth in claim 2, wherein the propylene and butylene oligomers are trimeric propylene, tetrameric propylene and diisobutylene.

* * * * *